(12) United States Patent
Ratti (10) Patent No.: US 8,114,401 B2
(45) Date of Patent: Feb. 14, 2012

(54) CHLAMYDIA TRACHOMATIS ANTIGENS

(76) Inventor: Giulio Ratti, Siena (IT)

( * ) Notice: Subject to any disclaimer, the term of this patent is extended or adjusted under 35 U.S.C. 154(b) by 0 days.

(21) Appl. No.: 12/586,601

(22) Filed: Sep. 24, 2009

(65) Prior Publication Data

US 2010/0098697 A1 Apr. 22, 2010

Related U.S. Application Data

(63) Continuation of application No. 11/272,051, filed on Nov. 14, 2005, now abandoned, which is a continuation of application No. 09/868,293, filed as application No. PCT/IB99/02065 on Dec. 17, 1999, now abandoned.

(30) Foreign Application Priority Data

Dec. 18, 1998 (GB) .................................. 9828000.1

(51) Int. Cl.
*A61K 39/00* (2006.01)
*A61K 39/118* (2006.01)
(52) U.S. Cl. ................. 424/139.1; 424/263.1; 424/184.1
(58) Field of Classification Search ......................... None
See application file for complete search history.

(56) References Cited

U.S. PATENT DOCUMENTS

| 6,822,071 | B1 | 11/2004 | Stephens et al. | |
| 7,041,490 | B1 * | 5/2006 | Griffais et al. | 435/252.3 |
| 7,575,913 | B2 * | 8/2009 | Griffais et al. | 435/252.3 |

FOREIGN PATENT DOCUMENTS

| WO | WO 95/28487 | 10/1995 |
| WO | 99/17741 | 4/1999 |
| WO | WO 99/28475 | 6/1999 |
| WO | WO 99/53948 | 10/1999 |
| WO | 01/40474 B2 | 6/2001 |
| WO | WO 02/082091 A2 | 10/2002 |

OTHER PUBLICATIONS

Greenspan et al. (Nature Biotechnology 17: 936-937, 1999).*
Hatch et al., Journal of Bacteriology, 1984; 157(1): 13-20.*
Allen, et al., "A Single Peptide From the Major Outer Membrane Protein of *Chlamydia trachomatis* Elicits T Cell Help for the Production of Antibodies to Protective Determinants," *Journal of Immunology* 147:674-679 (1991).
Anonymous Third Party observations filed under Article 115 EPC for European Patent Applications 99939279.8, 99939280.6, 99951023.3, 99954126.1; 99958455.0, 99960752.6, 99963037.9, 00901235.2, 00908862.6, 00925004.4, 00962125.1, 00962134.3, 00984741.9, 01928775.4, 01931274.3, 01954278.6, and 01959114.8, dated Mar. 23, 2006.
Bachrach, et al., "Brucella Ribosomal Protein L7/L12 Is a Major Component in the Antigenicity of Brucellin Inra for Delayed-Type Hypersensitivity in Brucella-Sensitized Guinea Pigs," *Infect. Immun.* 62:5361-5366 (1994).
Batteiger, et al., "Species- , Serogroup- , and Serovar-Specific Epitopes Are Juxtaposed in Variable Sequence Region 4 of the Major Outer Membrane Protein of Some *Chlamydia trachomatis* Serovars," *Infection and Immunity* 64:2839-2841 (1996).
Bini, et al., "Mapping of *Chlamydia trachomatis* Proteins by Immobiline-polyacrylamide Two-Dimensional Electrophoresis: Spot Identification by N-Terminal Sequencing and Immunoblotting," *Electrophoresis* 17:185-190 (1996).
Coles, et al., "Analysis of the Human Serological Response to *Chlamydia trachomatis* 60-KDA Proteins by Two," *FEMS Microbiol Lett* 65:299-303 (1991).
Engel, of al., "Cloning and Characterization of RNA Polymerase Core Subunits of *Chlamydia trachomatis* by Using the Polymerase Chain Reaction," *Journal of Bacteriology* 172:5732-5741 (1990).
GenBank Accession No. P38001 printout.
Goswami, et al., "Extensive Heterogeneity of the Protein Composition of *Chlamydia trachomatis* Following Serial Passage in Two Different Cell Lines," *J Gen Microbiol* 136:1623-1629 (1990).
Greenspan, et al., "Defining Epitopes: It's Not As Easy As It Seems," *Nature Biotechnology* 17:936-937 (1999).
Oliveira, et al., "Immunization of Mice With Recombinant L7/L12 Ribosomal Protein Confers Protection Against Brucella Abortus Infection," *Vaccine* 14:959-962 (1996).
Roop, et al., "Identification of an Immunoreactive Brucella Abortus HTRA Stress Response Protein Homolog," *Infect. Immun.* 62:1000-1007 (1994).
Sanchez-Campillo, et al., "Identification of Immunoreactive Proteins of *Chlamydia trachomatis* by Western Blot Analysis of a Two-Dimensional Electrophoresis Map With Patient Sera," *Electrophoresis* 20:2269-2279 (1999).
Stephens, et al., "Genome Sequence of an Obligate Intracellular Pathogen of Humans: *Chlamydia trachomatis*," *Science* 282:754-759 (1998).
GenBank AF087292.1 printout Jan. 12, 1999.
GenBank M31119.1 printout Apr. 26, 1993.
Gish, W., BLASTP 2 printout May 4, 2006.
Kahane, S., et al., "Cloning, Characterization and Sequence of a Novel 59-KDA Protein of *Chlamydia Trachomatis*," *Gene* 90:61-67 (1990).
Swiss-Prot P18584 printout May 31, 2011.

* cited by examiner

*Primary Examiner* — Vanessa L Ford
*Assistant Examiner* — Lakia Tongue (57) ABSTRACT

Proteins encoded by *Chlamydia trachomatis* which are immunogenic in humans as a consequence of infection have been identified using Western blots of two-dimensional electrophoretic maps. Several known immunogens were identified, as were proteins not previously known to be immunogens, and proteins not previously reported as expressed gene products.

1 Claim, 3 Drawing Sheets

```
                           SEQUENCE LISTING

<160> NUMBER OF SEQ ID NOS: 15

<210> SEQ ID NO 1
<211> LENGTH: 9
<212> TYPE: PRT
<213> ORGANISM: Chlamydia trachomatis

<400> SEQUENCE: 1

Ser Lys Glu Thr Phe Gln Arg Asn Lys
1               5

<210> SEQ ID NO 2
<211> LENGTH: 10
<212> TYPE: PRT
<213> ORGANISM: Chlamydia trachomatis

<400> SEQUENCE: 2

Thr Thr Glu Ser Leu Glu Thr Leu Val Glu
1               5                   10

<210> SEQ ID NO 3
<211> LENGTH: 18
<212> TYPE: PRT
<213> ORGANISM: Chlamydia trachomatis

<400> SEQUENCE: 3

Leu Ala Val Ser Ser Gly Asp Gln Glu Val Ser Gln Glu Asp Leu Leu
1               5                   10                  15

Lys Glu

<210> SEQ ID NO 4
<211> LENGTH: 12
<212> TYPE: PRT
<213> ORGANISM: Chlamydia trachomatis
<220> FEATURE:
<221> NAME/KEY: Xaa
<222> LOCATION: 1
<223> OTHER INFORMATION: Xaa is any amino acid

<400> SEQUENCE: 4

Xaa Pro Ala Gly Asn Pro Ala Phe Pro Val Ile Pro
1               5                   10
```

```
<210> SEQ ID NO 5
<211> LENGTH: 10
<212> TYPE: PRT
<213> ORGANISM: Chlamydia trachomatis

<400> SEQUENCE: 5

Ala Lys Thr Arg Thr Leu Lys Gly Asp Gly
1               5                   10

<210> SEQ ID NO 6
<211> LENGTH: 11
<212> TYPE: PRT
<213> ORGANISM: Chlamydia trachomatis

<400> SEQUENCE: 6

Ser Asp Ser Ser His Asn Leu Leu Tyr Asn Lys
1               5                   10

<210> SEQ ID NO 7
<211> LENGTH: 18
<212> TYPE: PRT
<213> ORGANISM: Chlamydia trachomatis

<400> SEQUENCE: 7

Val Leu Leu Tyr Ser Gln Ala Ser Trp Asp Gln Arg Ser Lys Ala Asp
1               5                   10                  15

Ala Leu

<210> SEQ ID NO 8
<211> LENGTH: 11
<212> TYPE: PRT
<213> ORGANISM: Chlamydia trachomatis
<220> FEATURE:
<221> NAME/KEY: Xaa
<222> LOCATION: 8
<223> OTHER INFORMATION: Xaa is Ala or Gln
<220> FEATURE:
<221> NAME/KEY: Xaa
<222> LOCATION: 10
<223> OTHER INFORMATION: Xaa is Val or Asp

<400> SEQUENCE: 8

Lys Ala Val Tyr Val Gln Asp Xaa Glu Xaa Gln
1               5                   10

<210> SEQ ID NO 9
<211> LENGTH: 9
<212> TYPE: PRT
<213> ORGANISM: Chlamydia trachomatis
<220> FEATURE:
<221> NAME/KEY: Xaa
<222> LOCATION: 3
<223> OTHER INFORMATION: Xaa is any amino acid
<220> FEATURE:
<221> NAME/KEY: Xaa
<222> LOCATION: 4
<223> OTHER INFORMATION: Xaa is any amino acid

<400> SEQUENCE: 9

Lys Asp Xaa Xaa Thr Asn Gly Gln Arg
1               5

<210> SEQ ID NO 10
<211> LENGTH: 10
<212> TYPE: PRT
<213> ORGANISM: Chlamydia trachomatis
<220> FEATURE:
<221> NAME/KEY: Xaa
```

```
<222> LOCATION: 8
<223> OTHER INFORMATION: Xaa is any amino acid
<220> FEATURE:
<221> NAME/KEY: Xaa
<222> LOCATION: 10
<223> OTHER INFORMATION: Xaa is Tyr or Gly

<400> SEQUENCE: 10

Met Ser Lys Gly Gly Gln Thr Xaa Asp Xaa
1               5                   10

<210> SEQ ID NO 11
<211> LENGTH: 10
<212> TYPE: PRT
<213> ORGANISM: Chlamydia trachomatis
<220> FEATURE:
<221> NAME/KEY: Xaa
<222> LOCATION: 1
<223> OTHER INFORMATION: Xaa is any amino acid
<220> FEATURE:
<221> NAME/KEY: Xaa
<222> LOCATION: 3
<223> OTHER INFORMATION: Xaa is any amino acid

<400> SEQUENCE: 11

Xaa Gln Xaa Glu Asn Gly Ile Val Gly Leu
1               5                   10

<210> SEQ ID NO 12
<211> LENGTH: 12
<212> TYPE: PRT
<213> ORGANISM: Chlamydia trachomatis

<400> SEQUENCE: 12

Met Pro Ala Gly Asn Pro Ala Phe Pro Val Ile Pro
1               5                   10

<210> SEQ ID NO 13
<211> LENGTH: 10
<212> TYPE: PRT
<213> ORGANISM: Chlamydia trachomatis
<220> FEATURE:
<221> NAME/KEY: Xaa
<222> LOCATION: 3
<223> OTHER INFORMATION: Xaa is Asp or Lys
<220> FEATURE:
<221> NAME/KEY: Xaa
<222> LOCATION: 6
<223> OTHER INFORMATION: Xaa is Lys or Phe

<400> SEQUENCE: 13

Val Ala Xaa Asn Ile Xaa Tyr Asn Glu Glu
1               5                   10

<210> SEQ ID NO 14
<211> LENGTH: 5
<212> TYPE: PRT
<213> ORGANISM: Chlamydia trachomatis

<400> SEQUENCE: 14

Leu Pro Val Gly Asn
1               5

<210> SEQ ID NO 15
<211> LENGTH: 8
<212> TYPE: PRT
<213> ORGANISM: Chlamydia trachomatis
<220> FEATURE:
<221> NAME/KEY: Xaa
<222> LOCATION: 6
```

```
<223> OTHER INFORMATION: Xaa is Ser or Ala
<220> FEATURE:
<221> NAME/KEY: Xaa
<222> LOCATION: 8
<223> OTHER INFORMATION: Xaa is Lys or Ser

<400> SEQUENCE: 15

Ser Glu Lys Arg Lys Xaa Asn Xaa
1               5
```

CHLAMYDIA TRACHOMATIS ANTIGENS

CROSS REFERENCE TO RELATED APPLICATIONS

This application is a continuation of application Ser. No. 11/272,051, filed Nov. 14, 2005 now abandoned, which is a continuation of application Ser. No. 09/868,293, filed Mar. 4, 2002 now abandoned, which is a U.S. 371 national phase application of PCT/IB99/02065, filed Dec. 17, 1999, which claims priority to Great Britain Serial No. 9828000.1, filed Dec. 18, 1998. All of the above applications are incorporated herein by reference in their entireties.

This invention relates to antigenic proteins from *Chlamydia trachomatis*. In particular, it relates to antigens which are recognised by antibodies from chronically infected or convalescent patient sera.

BACKGROUND

The *Chlamydia* are obligate intracellular parasites of eukaryotic cells which are responsible for endemic sexually transmitted infections, trachoma, infectious pneumonitis, and various other disease syndromes. They occupy an exclusive eubacterial phylogenic branch, having no close relationship to any other known organisms—they are classified in their own order (Chlamydiales) which contains a single family (Chlamydiaceae) which in turn contains a single genus (*Chlamydia*). Four chlamydial species are currently known—*C. trachomatis, C. pneumoniae, C. pecorum* and *C. psittaci* [eg. see reference 1]. A genome sequence of *C. trachomatis* (serovar D) has recently been published [2].

The human serovariants ("serovars") of *C. trachomatis* are divided into two biovariants ("biovars"). Serovars A-K elicit epithelial infections primarily in the ocular tissue (A-C) or urogenital tract (D-K). Serovars LI, L2 and L3 are the agents of invasive lymphogranuloma venereum (LGV).

Although chlamydial infection itself causes disease, it is thought that, in some patients, the severity of symptoms is due, in fact, to an aberrant host immune response. Failure to clear the infection results in persistent immune stimulation and, rather than helping the host, this results in chronic infection with severe consequences, including sterility and blindness [3].

In addition, the protection conferred by natural chlamydial infection, is usually incomplete, transient, and strain-specific.

Due to the serious nature of the disease there is a desire to provide suitable vaccines. These may be useful (a) for immunisation against chlamydial infection or against chlamydia-induced disease (prophylactic vaccination) or (b) for the eradication of an established chronic chlamydial infection (therapeutic vaccination). Being an intracellular parasite, however, the bacterium can generally evade antibody-mediated immune responses.

Various antigenic proteins have been described for *C. trachomatis*, and the cell surface in particular has been the target of detailed research [eg. 1,4]. These include, for instance, pgp3 [5, 6, 7], MOMP [8], Hsp60 (GroEL) [9] and Hsp70 (DnaK-like) [10]. Not all of these have proved to be effective vaccines, however, and it is an object of the invention to identify chlamydial antigens which elicit an immune response during natural infection, in order to provide antigens and immunogens suitable for use in vaccine development.

DESCRIPTION OF THE INVENTION

The invention is based on the identification of proteins encoded by *Chlamydia trachomatis* which are immunogenic in man as a consequence of infection.

The invention provides a *C. trachomatis* protein having the MW and pI characteristics of protein 5, 6, 7, 8, 9, 11, 13, 14, 15, 16, 17, 18, 20, 21, 22, 23, 24, 25, 26, 27, 28, 29, 30, 31 32, 33, 34, 35, 36, 37, 38, 39, 40, 41, 42, 43, 44, 45, 46, 47, 48, 49, 50, 51, 52, 53, 54, or 55, as set out in Table II on page 15.

These include proteins having, in the L2 strain of *C. trachomatis*, an N-terminal amino acid sequence disclosed in Table III on page 16.

The invention also provides proteins having sequence identity to these *C. trachomatis* proteins. Depending on the particular protein, the degree of identity is preferably greater than 50% (eg. 65%, 80%, 90%, 95%, 98%, 99% or more). These homologous proteins include mutants, allelic variants, serovariants, and biovariants. Identity between the proteins is preferably determined by the Smith-Waterman homology search algorithm as implemented in the MPSRCH program (Oxford Molecular), using an affine gap search with parameters gap open penalty=12 and gap extension penalty=1. Typically, 50% identity or more between two proteins is considered to be an indication of functional equivalence.

The invention further provides proteins comprising fragments of the *C. trachomatis* proteins of the invention. The fragments should comprise at least n consecutive amino acids from the proteins and, depending on the particular protein, n is 7 or more (eg. 8, 10, 12, 14, 16, 18, 20, 50, 100 or more). Preferably the fragments comprise an epitope from the protein.

The proteins of the invention can, of course, be prepared by various means (eg. recombinant expression, purification from cell culture, chemical synthesis etc.) and in various forms (eg. native, fusions etc.). They are preferably prepared in substantially isolated or purified form (ie. substantially free from other *C. trachomatis* or host cell proteins)

According to a further aspect, the invention provides antibodies which bind to these proteins. These may be polyclonal or monoclonal and may be produced by any suitable means.

According to a further aspect, the invention provides nucleic acid encoding the proteins and protein fragments of the invention. Nucleic acid having sequence identity to this nucleic acid is also provided. Depending on the particular nucleic acid, the degree of identity is preferably greater than 50% (eg. 65%, 80%, 90%, 95%, 98%, 99% or more).

Furthermore, the invention provides nucleic acid which can hybridise to this nucleic acid, preferably under "high stringency" conditions (eg. 65° C. in a 0.1×SSC, 0.5% SDS solution).

Fragments of this nucleic acid are also provided. The fragments should comprise at least n consecutive nucleotides from the sequences and, depending on the particular sequence, n is 10 or more (eg. 12, 14, 15, 18, 20, 25, 30, 35, 40 or more).

It should also be appreciated that the invention provides nucleic acid comprising sequences complementary to those described above (eg. for antisense or probing purposes).

Nucleic acid according to the invention can, of course, be prepared in many ways (eg. by chemical synthesis, from genomic or cDNA libraries, from the organism itself etc.) and can take various forms (eg. single stranded, double stranded, vectors, probes etc.).

In addition, the term "nucleic acid" includes DNA and RNA, and also their analogues, such as those containing modified backbones, and also peptide nucleic acids (PNA) etc.

According to a further aspect, the invention provides vectors comprising nucleic acid of the invention (eg. expression vectors) and host cells transformed with such vectors.

According to a further aspect, the invention provides compositions comprising protein, antibody, and/or nucleic acid according to the invention. These compositions may be suitable as immunogenic compositions (including vaccines), for instance, or as diagnostic reagents.

The invention also provides nucleic acid, protein, or antibody according to the invention for use as medicaments (eg. as vaccines) or as diagnostic reagents. In particular, the invention provides protein 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 (as set out in Table II on page 15) for use as a chlamydial immunogen. Whilst it is believed that some of the proteins described in Table II may be known per se, they have not been disclosed as being immunogenic.

The invention also provides the use of nucleic acid, protein, or antibody according to the invention in the manufacture of (i) a medicament for treating or preventing infection due to *Chlamydia*; (ii) a diagnostic reagent for detecting the presence of *Chlamydia* or of antibodies raised against *Chlamydia*; and/or (iii) a reagent which can raise antibodies against *Chlamydia*. The *Chlamydia* may be any species or strain, but is preferably *C. trachomatis*. In preferred embodiments, the invention provides a protein of the 55 proteins of Table II for use in such manufacture.

The invention also provides a method of treating a patient, comprising administering to the patient a therapeutically effective amount of nucleic acid, protein, and/or antibody according to the invention.

According to further aspects, the invention provides various processes.

A process for producing proteins of the invention is provided, comprising the step of culturing a host cell according to the invention under conditions which induce protein expression.

A process for producing protein or nucleic acid of the invention is provided, wherein the protein or nucleic acid is synthesised in part or in whole using chemical means.

A process for detecting nucleic acid of the invention is provided, comprising the steps of (a) contacting a nucleic probe according to the invention with a biological sample under hybridising conditions to form duplexes: and (b) detecting said duplexes.

A process for detecting proteins of the invention is provided, comprising the steps of: (a) contacting an antibody according to the invention with a biological sample under conditions suitable for the formation of an antibody-antigen complexes; and (b) detecting said complexes. Similarly, the invention provides a process for detecting anti-chlamydial antibodies in a sample, comprising the steps of: (a) contacting a protein according to the invention with a biological sample under conditions suitable for the formation of an antibody-antigen complexes; and (b) detecting said complexes.

The invention also provides kits comprising reagents suitable for use in these processes.

A kit is provided comprising a nucleic probe according to the invention and means for detecting duplexes formed by the probe. A kit is provided comprising an antibody according to the invention and means for detecting antibody-antigen complexes formed by the antibody. A kit is provided comprising a protein according to the invention and means for detecting antibody-antigen complexes formed by the protein.

For the avoidance of doubt, the term "comprising" encompasses "including" as well as "consisting" eg. a composition "comprising" X may consist exclusively of X or may include something additional to X, such as X+Y.

DESCRIPTION OF THE DRAWINGS

FIG. 2 shows typical immunoblots. The whole map area is shown. Major known immunogens are marked for easier comparison. For other spot identification, refer to FIG. 1 and table II. Blot A is from PID patient JO51 (MIF titre 256), and has a serum dilution 1:5000. Blot B is from patient JO35 (MIF titre 64) affected by secondary sterility, and has a serum dilution 1:2500. Blot C is similar to blot B, but is from patient JO52. Blot D is from PID patient JO31 (MIF titre 256), and gas a serum dilution 1:5000.

EXAMPLES

Human Sera

Sera (Table I) were obtained from women who had responded to a chlamydial infection of the genital tract. The seventeen sera (A . . . Q) were obtained from 4 cases of lower genital tract infection and 13 laparoscopically-confirmed cases of PID (pelvic inflammatory disease), including 2 cases of secondary sterility. All sera were positive for a standard microimmunofluorescence test (MIF) with purified *C. trachomatis* L2 elementary bodies [11], and confirmed as *C. trachomatis* immune sera by an ELISA test with the plasmid-encoded pgp3 antigen [5].

A group of 10 seronegative control sera from healthy blood donors was tested by immunoblotting in the same way, and using the same dilutions as for patient sera, in order to exclude the occurrence of non-specific reactions.

Most sera were obtained from the *Chlamydia* collection of the Biobanque de Picardie (Amiens, France). Some PID and control sera from healthy blood donors were obtained from the Ospedale Policlinico S. Orsola (Bologna, Italy).

Preparation of Protein Samples

Purified chlamydial cells were obtained as described in reference 12, by growing *C. trachomatis* strain L2/343/Bu in Vero cell cultures according to standard procedures, followed by two cycles of density gradient centrifugation [13]. The average protein concentration of the purified elementary body (EB) preparation was determined using a biuret assay. Aliquots (2 mg protein/ml) were stored in water at −20° C. for subsequent electrophoretic analysis. The cells used were mainly in the form of EBs—all known chlamydial antigens to date have been found in elementary bodies, rather than reticular bodies.

Separation of Chlamydial Proteins

Chlamydial proteins were separated using high resolution 2D electrophoresis, performed using the immobiline/polyacrylamide system, essentially as described in references 14 and 15.

For analytical gels, approximately 45 μg total elementary body protein was used per gel. For semipreparative gels (for microsequencing), approximately 1 mg protein was used. Aliquots of the EB proteins were pelleted by low-speed centrifugation and resuspended in 8M urea, 4% CHAPS (3-[(3-cholamidopropyl)dimethylammonium]-1-propane sulfonate), 40 mM Tris base, 65 mM dithioerythritol (DTE) and trace amounts of bromophenol blue.

Isoelectric focusing was carried out on immobiline strips providing a non-linear 3 to 10 pH gradient (IPG strips, Amersham Pharmacia Biotech). Voltage was linearly increased from 300 to 3500 V during the first three hours, then stabilised at 5000 V for 22 hours (total Volts-hour product=110 kVh). After electrophoresis. IPG strips were equilibrated for 12 min against 6 M urea, 30% glycerol, 2% SDS, 0.05 M Tris.HCl, pH 6.8, and 2% DTE. The second dimension was carried out in a Laemmli system on 9-16% polyacrylamide linear gradient gels (18 cm×20 cm×1.5 mm), at 40 mA/gel constant current, for approximately 5 hours until the dye front reached the bottom of the gel. Analytical gels were stained with ammoniacal silver nitrate [16]. The protein maps were scanned with a laser photodensitometer (Molecular Dynamics) and converted into electronic files which were then analysed with the Melanie II computer software (Bio-Rad).

Figure 1:
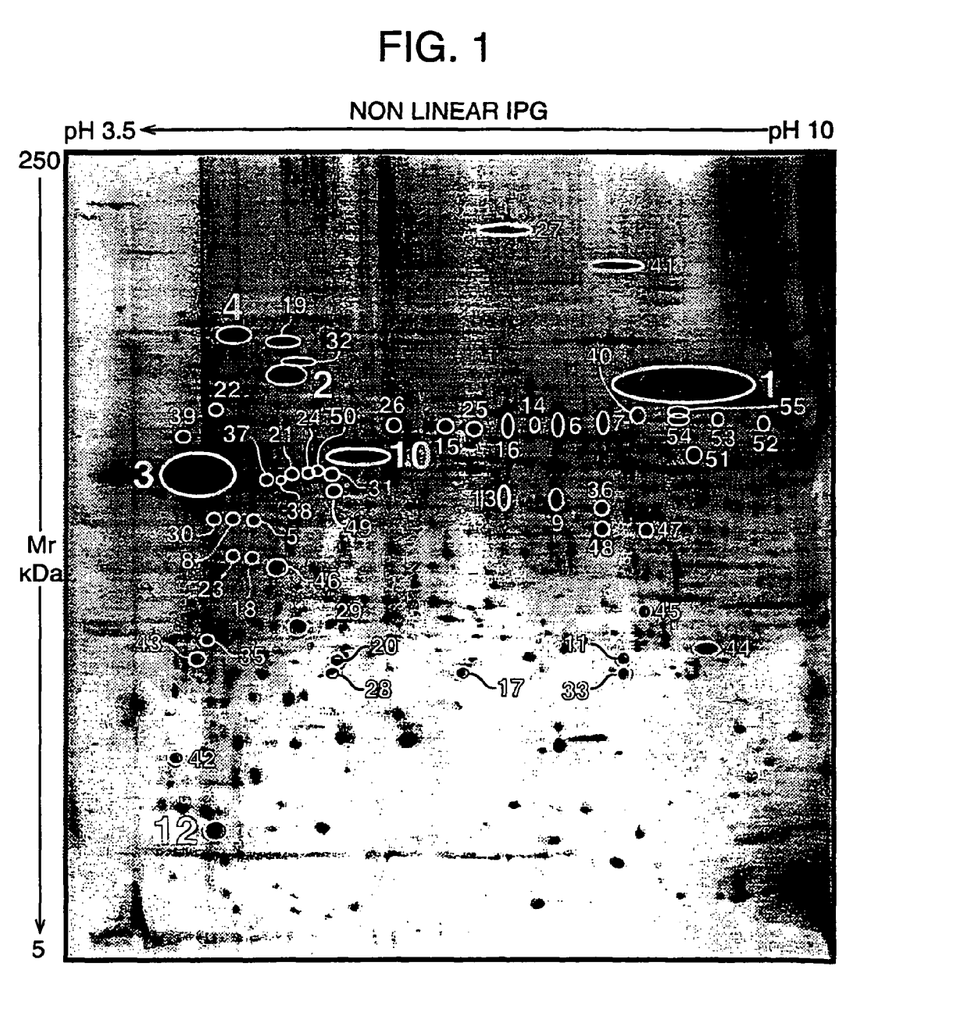
FIG. 1 shows the annotated reference 2D electrophoretic EB map, also indicating the positions of the immunoreactive protein spots labelled 1-55. Groups of spots which appear to be an isoelectric series of the same protein are encircled together and classified under the same identification number.
Figure 2A:
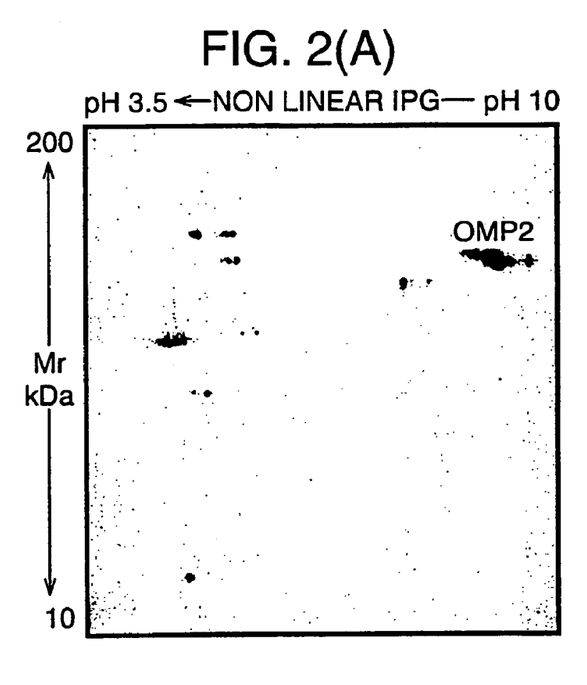
Figure 2B:
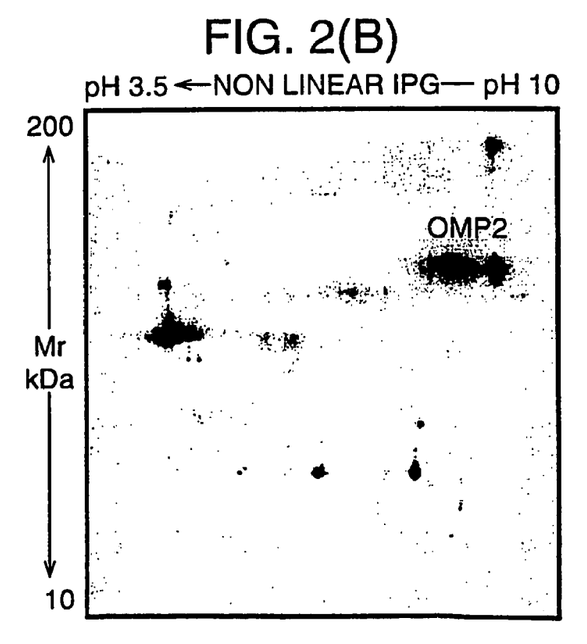
Figure 2C:
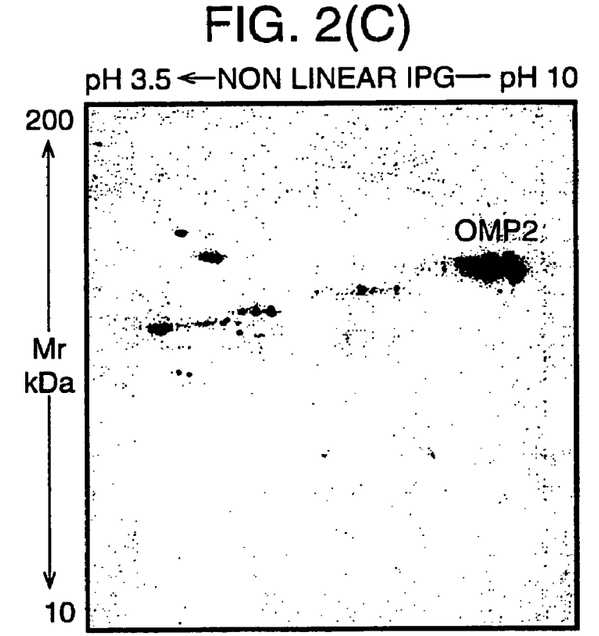
Figure 2D:
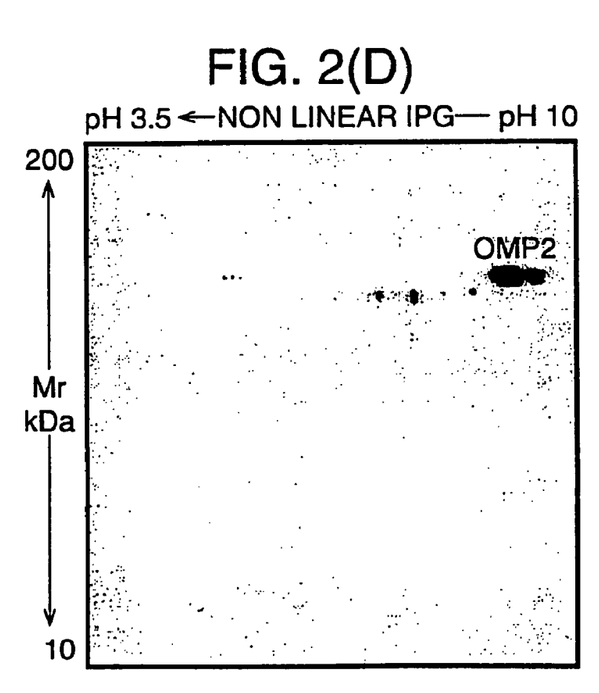

FIG. 1 shows the annotated reference EB map which was used to identify proteins on immunoblots. MW and pI coordinates for the reference map were calibrated by co-migration of the chlamydial proteins with human serum proteins acting as reference proteins. The isoelectric point values used for serum proteins were those described in reference 17.

Immunoblot Analysis

Immunoblotting results are summarized in FIG. 2 and Table II.

After two-dimensional electrophoresis, the gels were electroblotted onto nitrocellulose membranes [18], and processed according to standard procedures, modified as described in reference 19. Briefly, before immunodetection, the membranes were stained in 0.2% (w/v) Ponceau S in 3% (w/v) trichloroacetic acid for 3 minutes and the positions of selected anchor spots were marked on the blot to assist matching of the immunoblots with the silver stained map. Immunoreactive spots were detected by overnight incubation at room temperature with patient sera (1500-5000× dilutions), followed by incubation with rabbit anti-human IgGs conjugated with peroxidase (Cappel, 7000× dilution), and detection with a chemiluminescence based kit (Pharmacia Amersham Biotech).

Typically, six identical 2D maps were prepared in parallel for each experiment—five were blotted onto nitrocellulose and one was stained with silver nitrate for subsequent correlation with the immunoblots and computer-assisted matching to the reference map.

The spot signals on the immunoblot almost always corresponded to a spot on the silver stained gel. However, in at least two instances (spots 13 and 14 in FIG. 1), immunoblot analysis detected protein spots which were not visible in the silver stained map. This shows that this technique has a superior sensitivity and should be taken into consideration as a valuable tool also for systematic proteomics studies.

To assist matching of the immunoblot with the reference map shown in FIG. 1, the nitrocellulose blots were marked with a number of internal "anchor" spots using transient Ponceau Red staining. After incubation with the sera and detection of bound antibodies by chemiluminescence, the immunoblot images were matched to the reference map and spots were assigned the corresponding pI and MW coordinates (see Table II). When the position and shape of the spot (or isoelectric series of spots) coincided with a previously-identified EB antigen, an immune response against such antigen was recorded. In all other cases the immunoblot spot was identified by the MW and pI coordinates taken at the baricentre of the stained area (or the coordinate range, in the case of complex spot patterns). It will be appreciated that the MW and pI values are determined electrophoretically, and may have a potential average error of +/−10%. The higher MW measurements will tend to be less accurate.

While control blots were totally blank, patient blots showed individually different patterns comprising a number of spots, which varied from 2 to 28, with an average of around 15 (see Table II). The number of immunoreactive spots had did not correlate with the serum MIF titres (see Tables I and II), so blot patterns appear to reflect a real individual variation in humoral responses, and not just the difference of antibody titres. This was also confirmed by comparing the results of each serum at various dilutions.

Typical immunoblot results are shown in FIG. 2. The only constant feature for all examined sera was the presence of antibodies against a complex cluster of spots previously identified as due to the cysteine-rich outer membrane protein OMP2 [12]. This cluster is shown as spot 1 in FIG. 1—all the spots labelled "1" were scored as a single antigen, but a number of accessory spots with lower MW and pI values which usually appear associated to OMP2 reactivity were separately scored, as their relationship to the OMP2 polypeptide is still unclear. Because the OMP2 protein is chlamydia-specific, and does not seem to undergo any relevant antigenic variation, it can be considered probably the best marker of chlamydial infection in this study.

The next-most frequent spots which were observed correspond to the following:

Spot 2—the GroEL-like (hsp60) protein (15/17 patients)
Spot 3—the major outer membrane protein MOMP (13/17 patients)
Spot 4—the DnaK-like (hsp70) protein (11/17 patients).

Reactivity with these known immunogens can be considered as an internal control which demonstrates the quality of the human sera used in this study. The lack of pgp3 reactivity on the blots, however, is significant because all the sera had been found positive in an ELISA confirmatory assay with a purified soluble form of pgp3. This suggests that antibody response to pgp3 in human infections occurs mainly against epitopes available only in a correctly folded protein structure, which would be lost in these experiments.

Patient immune reactions were also detected against the following proteins [cf. ref. 12]:

Spot 10—protein elongation factor EF-Tu (8/17)
Spot 19—ribosomal proteins S1 (5/17)
Spot 12—ribosomal protein L7/L12 (7/17)

Besides these known proteins, several new immunoreactive proteins were detected with frequencies ranging from 11/17 down to 1/17. The MW and pI characteristics of these proteins are shown in Table II. In addition, in a few cases, further analysis was performed by N-terminal amino acid sequencing supplemented with database homology searches.

Spot Microsequencing 2D maps were prepared as described above, starting from 1 mg total EB protein per run, followed by blotting onto polyvinylidene difluoride membranes (BioRad PVDF membranes 20×20 cm, 0.2 micron pore size), as in reference 20. The blots were stained with 0.1% (w/v) Coomassie Brilliant Blue R250 in 50% aqueous methanol for 5 minutes, and de-stained in 40% methanol, 10% acetic acid. Membranes were dried at 37° C. and stored at −20° C. for further analysis. Selected protein spots were cut out and submitted to amino acid sequencing by Edman degradation using an automatic Protein/Peptide Sequencer (mod 470A; Applied Biosystem Inc.) connected on-line with a phenylthiohydantoin-amino acid analyser model 120A and a control/Data Module model 900A (Applied Biosystems Inc.). Typically 3 or 4 equivalent spots from similar blots were used, according to the estimated relative molar amount of protein in the spot.

The results of the sequencing are shown in Table III on page 16.

Computer Analysis of Sequences

Using the N-terminal sequence data, database searches for protein similarity were performed using the BLAST program [21] available from NCBI website and programs of the GCG software (Wisconsin Package Version 9.0) [22]. Theoretical pI and MW values were calculated by the pI/MW computer program available from the ExPASy internet server.

In addition to the usual databases, the genomic sequencing data of the *C. trachomatis* D/UW-3/Cx strain provided by the *Chlamydia* Genome Project [http://chlamydia-www.berkeley.edu:4231] was searched. Although the present study used a *C. trachomatis* serovar L2 strain (lymphogranuloma biovar), which has a different pathogenicity phenotype, several protein sequences could be safely correlated to the serovar D genes.

These searches with N-terminal data allowed the correlation of seven immunoreactive spots to known sequences (in addition to the seven noted above):

Spot 15: predicted to be a periplasmic peptidase (currently annotated in the serovar D genomic database as htrA).

Spots 18 & 46: predicted to be an outer membrane protein (currently annotated in the genomic database as ompB).

Spot 21: Although the amino acid sequence does not match any previously-described proteins, it shows homology to an internal sequence from EF-Tu. This protein may be a breakdown or processing product of EF-Tu, or a variant.

Spot 24: the RNA polymerase alpha subunit (rpoA)

Spot 25: homologous to bacterial leucine peptidases (currently annotated in the genomic database as pepA).

Spot 38: predicted to be a GTP-binding protein (currently annotated as ychF).

The N-terminal sequences of spots 26, 31 and 33 do not match any database sequences, including the published serovar D sequence.

Table IV shows a summary of identifications (some putative) of several immunoreactive antigens, which were obtained either by comparison with previous 2D mapping data, or by homology searches with the N-terminal sequencing data obtained above.

Proteins of Particular Interest

Of particular interest are the following proteins identified from the immunoblots:

Spot 24

This spot is believed to be the alpha chain of the *C. trachomatis* RNA polymerase (gi620029), based on its MW/pI position, and on its N-terminus sequence. Although the RNAP alpha chain has previously been described [23], it has never been reported as a chlamydial immunogen. Four patients showed reactivity to this protein, demonstrating that it is immunogenic in humans as a consequence of chlamydial infection. Whilst the intracellular parasitic nature of *Chlamydia* means that it can generally evade antibody-mediated immune responses, the antibody reactivity demonstrated above indicates that the immune system does encounter these proteins during natural infection, and the formation of antibodies may, for instance, also help to prime the T-cell-mediated immune responses.

Spots 18 & 46

Spots 18 and 46 appear to be homologous to the ompB gene in the serotype D genome, annotated as encoding a putative outer membrane protein. The N-terminal sequences and pI & MW values (at least for spot 18-5.08/34.09 vs predicted theoretical values of 5.06/34.5) are in agreement with the expected properties of an ompB gene product, after cleavage of the predicted N-terminal signal peptide.

It has also been found that that both spot 46 and 18 are present in a 2D electrophoretic map of a purified preparation of chlamydial outer membrane complex, which also supports the view that spots 18 and 46 represent the homologs of the serotype D ompB gene.

The reason why this protein appears as two distinct electrophoretic species was not investigated, but a spot shift of this type is usually associated to a variation of amino acid composition, either due to amino acid sequence variation, and/or to true or artifactual derivatisation of some amino acid residues.

Five patients showed reactivity to this protein, demonstrating that it is immunogenic in humans as a consequence of chlamydial infection.

Spot 25

This spot is believed to be an aminopeptidase, based on its MW/pI position and on its N-terminus sequence (both in comparison with the published serovar D sequence pepA). Four patients showed reactivity to this protein, demonstrating that it is immunogenic in humans as a consequence of chlamydial infection.

Spot 38

This spot is believed to be a GTP-binding protein, based on its MW/pI position and on its N-terminus sequence (both in comparison with the published serovar D sequence ychF). Two patients showed reactivity to this protein, demonstrating that it is immunogenic in humans as a consequence of chlamydial infection.

Spot 15

This spot is believed to be a stress-induced protease, based on its MW/pI position and on its N-terminus sequence (both in comparison with the published serovar D sequence htrA). Seven patients showed reactivity to this protein, demonstrating that it is immunogenic in humans as a consequence of chlamydial infection.

Spot 8

Nine patients showed reactivity towards protein spot 8, which could not be characterised by N-terminal sequencing. It does, however, have the following 'constellation type 2' amino acid composition (molar percentages):

| aa | % |
|---|---|
| Ala | 6.5 |
| Arg | 3.5 |
| Asx | 8.4 |
| Glx | 12.5 |
| Gly | 22.5 |
| His | 0.5 |
| Ile | 3.7 |
| Leu | 6.7 |
| Lys | 3.7 |
| Met | 0.5 |
| Phe | 2.8 |
| Pro | 3.4 |
| Ser | 13.7 |
| Thr | 5.1 |
| Tyr | 2.2 |
| Val | 4.3 |

Cys and Trp are not determined in this type of analysis, and it is not possible to distinguish between Glu/Gln and Asp/Asn.

Inability to obtain N-terminal sequence, despite repeated attempts, suggests that the N-terminal residue is blocked due to some form of modification (eg. a lipoprotein). Modification is often a characteristic of membrane-associated proteins in eukaryotes, but is also a characteristic of outer surface proteins or secreted proteins in bacterial species (eg. lipoproteins [24], mycoplasma outer membrane proteins [25], the FHA virulence factor of. *B. pertussis* [26] etc.).

Spot 12

This spot is believed to be due to the ribosomal protein L7/L12. Seven patients showed reactivity to this protein, demonstrating that it is immunogenic in humans as a consequence of chlamydial infection. Although this protein has previously been described in chlamydia [accession number P38001], it has never been reported as a chlamydial immunogen. It has, however, been described as an immunogen in *Brucella* infections [27,28].

Spot 19

This spot is believed to be due to the ribosomal protein S1. Five patients showed reactivity to this protein, demonstrating that it is immunogenic in humans as a consequence of chlamydial infection. Although this protein has previously been described in chlamydia [accession number P38016], it has never been reported as an immunogen.

Spot 10

This spot is believed to be due to the protein synthesis elongation factor EF-Tu. Eight patients showed reactivity to this protein, demonstrating that it is immunogenic in humans as a consequence of chlamydial infection. Although the chlamydial EF-Tu has previously been described [accession number P26622], it has never been reported as an immunogen.

Spots 10, 12, 15, 19 & 24

Given the importance, in chronic infections, of a possible previous sensitisation to conserved microbial antigens that may trigger immunopathogenic reactions, it is noteworthy that several of these new immunoreactive antigens belong to conserved families of bacterial proteins: four (23%) sera reacted with spot 24 (the alpha subunit of the RNA polymerase); five (29%) recognised spot 19 (ribosomal protein S1); eight (47%) recognised spot 10 (EF-Tu); seven (41%) recognised spot 15 (putative stress-induced protease of the HtrA (S2C peptidase) family); and seven sera (41%) recognised spot 12 (the ribosomal protein L7/L12). In the group of sera used in this study, 12/17 (70.6%) reacted with at least one of these five antigens and, including the hsp60 and hsp70 antigens, all sera had antibodies reacting with between 1 and 7 (average 3.7) chlamydial proteins which have homologs in other bacteria.

Theories which postulate a role for immunological sensitisation mechanisms in chlamydial pathology, as described for the hsp60 GroEL-like antigen [29], should in fact be extended to several other common bacterial antigens, which may be immunogenic in other bacterial infections. For instance the protein elongation factor EF-Tu is immunogenic during the acute phase of infection with *Haemophilus influenzae*, and both L7/L12 and the HtrA stress-induced protease homologues are immunogenic in *Brucella* infections. In the case of EF-Tu, the abundance of this protein in the bacterial cell may favour its "visibility" by the immune system. It should be noted, however, that EF-Tu has been described as associated to outer membrane and periplasmic cell fractions [30], and more recently data suggest that EF-Tu, in addition to its function in peptide elongation, has also a chaperone activity implicated in protein folding and protection from stress [31]. Particularly intriguing is the response to the L7/L12 ribosomal protein, since in *Brucella melitensis* infections the homologous L7/L12 antigen induces a DTH cell-mediated response [27]. Furthermore vaccination of BALB/c mice with L7/L12 was shown to give protection against infection by *B. abortus* [32]. The unexpected finding that antibodies to L7/L12 are fairly frequent in patients infected by *C. trachomatis* suggests that perhaps further attention should be paid to this antigens also in chlamydia-induced disease.

Spots 5, 6, 7, & 9

These proteins, whilst not yet correlated with any available genome sequence, and not yet having been sequenced, are of obvious interest given their prevalence (>50%) in the sera tested.

It will be understood that the invention is described above by way of example only and modifications may be made whilst remaining within the scope and spirit of the invention.

TABLE I

SUMMARY OF PATIENT SERA

The letters in the first column correspond to those given in Table II. The codes in the second column refer to the original serum collection. The pathology associated with each patient is broadly indicated as cervicitis (lower genital tract infection), PID or sterility (secondary to infection). All sera were characterised by MIF assay with purified L2 elementary bodies. The MIF titre given in the table is the highest two-fold dilution which gave a positive signal. The 'Best Dilution' is the dilution which was found to give minimum background without loss of signal on weaker spots.

| Serum ID in Table II | Original Serum ID | Pathology | MIF titre | Best Dilution |
|---|---|---|---|---|
| A | JO45/7931 BB | cervicitis | 256 | 1:5000 |
| B | JO28/7935 BB | cervicitis | 16 | 1:1500 |
| C | JO29/7936 BB | cervicitis | 16 | 1:2000 |
| D | JO51/7997 BB | cervicitis | 256 | 1:5000 |
| E | hs-C (Bologna) | P.I.D. | 256 | 1:5000 |
| F | 14293 BB | P.I.D. | 1024 | 1:10000 |
| G | hs-B (Bologna) | P.I.D. | 32 | 1:2000 |
| H | JO6/7942BB | P.I.D. | 256 | 1:5000 |
| I | JO17/7953 BB | P.I.D. | 256 | 1:5000 |
| J | JO43/7989 | P.I.D. | 256 | 1:5000 |
| K | JO20=/7956 BB | P.I.D. | 256 | 1:5000 |
| L | JO42/7988 BB | P.I.D. | 256 | 1:5000 |
| M | JO41/7987 BB | P.I.D. | 256 | 1:5000 |
| N | JO31/7977 BB | P.I.D. | 256 | 1:5000 |
| O | 13839 BB | P.I.D. | 256 | 1:5000 |
| P | JO35/7934 BB | sterility | 64 | 1:2500 |
| Q | JO52/7933 BB | sterility | 64 | 1:2500 |

TABLE II

PATIENT REACTIVITY WITH PROTEIN SPOTS

| Spot # | pI | MW | A | B | C | D | E | F | G | H | I | J | K | L | M | N | O | P | Q | FREQ |
|---|---|---|---|---|---|---|---|---|---|---|---|---|---|---|---|---|---|---|---|---|
| 1 | complex | | + | + | + | + | + | + | + | + | + | + | + | + | + | + | + | + | + | 17 |
| 2 | 5.2-5.3 | 59.7 | + | + | + | + | + | + | + | + | + | + | | | + | + | + | + | + | 15 |
| 3 | 4.6-4.9 | 40 | + | + | + | + | + | + | + | | + | + | | + | | + | + | | + | 13 |
| 4 | 4.92-5.04 | 70.5 | + | + | + | + | + | + | | | + | + | + | | + | | | | + | 11 |
| 5 | 5.09 | 36.6 | + | + | | + | + | + | | | + | + | | | | + | | + | + | 11 |
| 6 | 6.34 | 46.2-50 | + | | | + | + | + | | | + | + | + | | | + | | + | + | 10 |
| 7 | 6.59 | 46.2-50.2 | + | | | + | + | + | | | + | + | + | | | + | | + | + | 10 |

TABLE II-continued

PATIENT REACTIVITY WITH PROTEIN SPOTS

| Spot # | pI | MW | A | B | C | D | E | F | G | H | I | J | K | L | M | N | O | P | Q | FREQ |
|---|---|---|---|---|---|---|---|---|---|---|---|---|---|---|---|---|---|---|---|---|
| 8 | 4.96 | 36.6 | + | | + | | + | + | | | + | + | | | | + | | + | + | 9 |
| 9 | 6.36 | 37.7-39.4 | + | + | | | + | + | | | + | + | + | | | | | + | + | 9 |
| 10 | 5.44-5.64 | 42.2 | + | + | + | | + | | + | | | + | | | | | | + | + | 8 |
| 11 | 6.66 | 26.1 | | + | | | + | + | | | + | | + | | | + | + | | + | 8 |
| 12 | 4.80 | 15.8 | | + | | + | + | | | | + | | + | + | | | | | | 6 |
| 13 | 6.1 | 37.4-39.2 | + | + | | | + | | | | | | + | | | + | | + | + | 7 |
| 14 | 6.24 | 47.9 | + | | | | + | + | | | + | + | + | | | | | + | | 7 |
| 15 | 5.89 | 48.4 | + | + | + | | + | + | | | | | + | | | | | + | | 7 |
| 16 | 6.15 | 46-50 | + | | | | + | | | | + | + | + | | | | | + | + | 7 |
| 17 | 5.92 | 25.3 | | + | | | + | + | | | | | | | | + | + | | + | 6 |
| 18 | 5.08 | 34.09 | | | + | + | + | | | | + | | | | | | | | + | 5 |
| 19 | 5.14-5.28 | 69 | + | | + | + | + | | | | + | | | | | | | | | 5 |
| 20 | 5.44 | 26.2 | | + | | | + | | | | | | | | | + | + | | + | 5 |
| 21 | 5.27 | 40.5 | | + | + | + | | | | | + | | | | | | | | + | 5 |
| 22 | 4.81 | 46.3 | + | | + | | | | | | + | + | + | | | | | | | 5 |
| 23 | 4.97 | 34.2 | | | | + | | + | | | + | | | | | | | | | 4 |
| 24 | 5.32 | 40.5 | | | + | + | | | | | + | | | | | | | | | 4 |
| 25 | 5.97 | 47.6 | + | + | | | | | | | | | | | | | | + | + | 4 |
| 26 | 5.68 | 48.6 | + | | | | | + | | | | | + | | | | | | + | 4 |
| 27 | 6.29-6.42 | 124.5 | + | | | | + | | | | | + | | | | | | + | | 4 |
| 28 | 5.39 | 25.5 | | | | + | + | | | | | | | | | + | | | | 3 |
| 29 | 5.1 | 28.7 | | | | + | | | | | + | | | | | + | | | | 3 |
| 30 | 4.8 | 36.7 | | | + | + | | | | | | | | | | | | + | | 3 |
| 31 | 5.43 | 40.4 | | | | + | | | | | | | + | | | | | | + | 3 |
| 32 | 5.2-5.37 | 62.4 | | | + | | + | | | | | | + | | | | | | | 3 |
| 33 | 6.64 | 25.4 | | | | | + | | | | + | | | | | | | | | 2 |
| 34 | 4.79 | 28.1 | | | | + | | | | | | | | | | | | + | | 2 |
| 35 | 4.82 | 29.5 | | | | + | | | | | | | | | | | | | + | 2 |
| 36 | 6.55 | 37.5 | | | | | + | | | | | + | | | | | | | | 2 |
| 37 | 5.14 | 40.3 | | | + | | | | | | | | | | | | | | + | 2 |
| 38 | 5.23 | 40.1 | | | | | | | | | | | | | | | | + | + | 2 |
| 39 | 4.69 | 45.7 | | | + | | | | | | | | | + | | | | | | 2 |
| 40 | 6.89 | 50 | | | | | | | | | | + | | | | | | + | | 2 |
| 41 | 6.39-6.55 | 105 | + | | | | + | | | | | | | | | | | | | 2 |
| 42 | 4.57 | 20.3 | | | | | | | | | + | | | | | | | | | 1 |
| 43 | 4.72 | 26.5 | | | | | + | | | | | | | | | | | | | 1 |
| 44 | 7.6 | 26.95 | | | | | | | | | | | + | | | | | | | 1 |
| 45 | 6.9 | 29.7 | | | | | | | | | | | | | | + | | | | 1 |
| 46 | 5.19 | 33.4 | | | | + | | | | | | | | | | | | | | 1 |
| 47 | 6.99 | 35.8 | | | | | | | | | | | + | | | | | | | 1 |
| 48 | 6.54 | 35.8 | | | | | | | | | | | + | | | | | | | 1 |
| 49 | 5.44 | 39.0 | | | | | | | | | | | | | | | | + | | 1 |
| 50 | 5.37 | 41.0 | | | | | | | | | | | | | | | | + | | 1 |
| 51 | 7.59 | 42.6 | | | | | | | | | | | + | | | | | | | 1 |
| 52 | 8.73 | 49.2 | | | | | + | | | | | | | | | + | | | | 1 |
| 53 | 7.98 | 49.4 | | | | + | | | | | | | | | | | | | | 1 |
| 54 | 7.4 | 50.2 | | | | | | | | | | | + | | | | | | | 1 |
| 55 | 7.4 | 51.5 | | | | | | | | | | | + | | | | | | | 1 |

TABLE III

N-TERMINAL SEQUENCES OF PROTEINS

| Spot # | N-terminal sequence |
|---|---|
| 10 | SKETFQRNK |
| 12 | TTESLETLVE |
| 15 | LAVSSGDQEVSQEDLLKE |
| 18 | XPAGNPAFPVIP |
| 21 | AKTRTLKGDG |
| 24 | SDSSHNLLYNK |
| 25 | VLLYSQASWDQRSKADAL |
| 26 | KAVYVQD(A/Q)E(V/D)Q |
| 31 | KDxxTNGQR |
| 33 | MSKGGQtxD(Y/G) |
| 38 | XQXENGIVGL |
| 46 | MPAGNPAFPVIP |

TABLE IV

IDENTIFICATION OF ANTIGENS

| spot | Map location | N-terminal AA seq | Annotation | CT-D gene | Predicted pI/MW |
|---|---|---|---|---|---|
| 1 | OMP2 cluster | — | OMP2 | omcB | 7.65-7.92/54.5-58.7 |
| 2 | 5.2-5.3/59.7 | VA(D/K)NI(K/F)YNEE | GroEL-like | groEL1 | 5.11/58.1 |
| 3 | 4.6-4.9/40 | LPVGN | MOMP | ompA | 4.69/40.3 |
| 4 | 4.92-5.04/70.5 | SEKRK(S/A)N(K/S).... | DnaK-like | dnaK | 4.88/70.7 |
| 10 | 5.44-5.64/42.2 | SKETFQRNK | EF-Tu | tufA | 5.36/43.1 |
| 12 | 4.80/15.8 | TTESLETLVE | Ribosomal protein L7/12 | rl7 | 5.09/13.5 |
| 15 | 5.89/48.4 | LAVSSGDQEVSQEDLLKE | stress induced protease | htrA | 5.83/49.5 |
| 18 | 5.08/34.09 | XPAGNPAFPVIP | outer membrane protein | ompB | 5.06/34.5 |
| 19 | 5.14-5.28/69 | Not determined | Ribosomal protein S1 | rs1 | 5.17/63.6 |
| 21 | 5.27/40.5 | AKTRTLKGDG | EF-Tu related peptide? | — | — |
| 24 | 5.32/40.5 | SDSSHNLLYNK | RNAP alpha chain | rpoA | 5.34/41.7 |
| 25 | 5.97/47.6 | VLLYSQASWDQRSKADAL | Aminopeptidase | pepA | 5.74/54.0 |
| 26 | 5.68/48.6 | KAVYVQD(A/Q)E(V/D)Q | Not identified | — | — |
| 31 | 5.43/40.4 | KDxxTNGQR | Not identified | — | — |
| 33 | 6.64/25.4 | MSKGGQtxD(Y/G) | Not identified | — | — |
| 38 | 5.23/40.1 | XQXENGIVGL | GTP-binding protein | ychF | 5.16/39.5 |
| 46 | 5.19/33.4 | MPAGNPAFPVIP | outer membrane protein | ompB | 5.06/34.5 |

"CT-D gene" refers to the gene name from reference 2 and gives the names of genes likely to encode homologue proteins in C. trachomatis D.
Theoretical pI/MW values in the last column, to be compared to the experimental values, were calculated the from CT-D gene sequences.

REFERENCES

The Contents of which are Incorporated herein in their Entirety

1 Raulston (1995) Chlamydial envelope components and pathogen-host cell interactions. Mol Microbiol 15(4):607-616.
2 Stephens et al. (1998) Genome Sequence of an Obligate intracellular Pathogen of Humans: Chlamydia trachomatis. Science 282:754-759.
3 Ward (1995) The immunobiology and immunopathology of chlamydial infections. Apmis. 103:769-96.
4 Moulder (1991) Interaction of Chlamydiae and host cells in vitro. Microbiol Rev 55(1):143-190.
5 Comanducci et al. (1994) Humoral immune response to plasmid protein pgp3 in patients with Chlamydia trachomatis infection. Infect Immun 62(12):5491-5497.
6 EP-A-0499681
7 WO95/28487
8 Murdin et al. (1993) Infect Immun 61:4406-4414
9 Cerrone et al. (1991) Cloning and sequence of the gene for heat shock protein 60 from Chlamydia trachomatis and immunological reactivity of the protein. Infect Immun 59(1):79-90.
10 Raulston et al. (1993) Molecular characterization and outer membrane association of a Chlamydia trachomatis protein related to the hsp70 family of proteins. J. Biol. Chem. 268:23139-23147.
11 Wang & Grayston (1970) Immunologic relationship between genital TRIC, lymphogranuloma venereum, and related organisms in a new microtiter indirect immunofluorescence test. Am. J. Opthalmol. 70:367-374
12 Bini et al. (1996) Mapping of Chlamydia trachomatis proteins by immobiline-polyacrylamide two-dimensional electrophoresis: spot identification by N-terminal sequencing and immunoblotting. Electrophoresis 17:185-190.
13 Schacter & Wyrick (1994) Culture and isolation of Chlamydia trachomatis. Meth Enzymol 236:377-390
14 Görg et al. (1988) The current state of two-dimensional electrophoresis with immobilized pH gradients. Electrophoresis 9:531-546
15. Hochstrasser et al. (1988) Methods for increasing the resolution of two-dimensional protein electrophoresis. Anal. Biochem. 173:424-435.
16 Oakley et al. (1980) A simplified ultrasensitive silver stain for detecting proteins in polyacrylamide gels. Anal. Biochem. 105:361-363.
17 Bjellqvist et al. (1993) A nonlinear wide-range immobilized pH gradient for two-dimensional electrophoresis and its definition in a relevant pH scale. Electrophoresis 14: 1357-1365
18 Towbin et al. (1979) Electrophoretic transfer of proteins from polyacrylamide gets to nitrocellulose sheets: procedure and some applications. Proc Natl Acad Sci USA 76: 4350-4354.
19 Magi et al. Chapter entitled "Immunoaffinity identification of 2-DE separated proteins" in Methods in Molecular Biology, 2-D Proteome analysis protocols. AJ Link (ed.), Humana Press, Totowa, N.J., USA.
20 Matsudaira (1987) Sequence from picomole quantities of proteins electroblotted onto polyvinylidene difluoride membranes. J Biol Chem 262:10035-10038.

21 Altschul et al. (1990) Basic local alignment search tool. *J Mol Biol* 215:403-410.
22 Devereux et al. (1984) A comprehensive set of sequence analysis programs for the VAX. *Nucleic Acids Res* 12: 387-395.
23 Gu et al. (1995) *Chlamydia trachomatis* RNA polymerase alpha subunit: sequence and structural analysis. *J Bacteriol* 177:2594-2601.
24 Nystrsm et al. (1992) Membrane protein acylation. Preference for exogenous myristic acid or endogenous saturated chains in *Acholeplasma laidlawii*. *Eur J Biochem* 204:231-40
25 Jan et al. (1995) Acylation and immunological properties of *Mycoplasma gallisepticum* membrane proteins. *Res Microbiol* 146:739-50
26 Lambert-Buisine et al. (1998) N-terminal characterization of the *Bordetella pertussis* filamentous haemagglutinin. *Mol Microbial* 28:1283-93
27 Bachrach et al. (1994) *Brucella* ribosomal protein L7/L12 is a major component in the antigenicity of brucellin INRA for delayed-type hypersensitivity in *Brucella*-sensitized guinea pigs. *Infect. Immun.* 62:5361-5366
28 Roop et al. (1994) Identification of an immunoreactive *Brucella abortus* HtrA stress response protein homolog. *Infect. Immun.* 62:1000-1007
29. Morrison et al. (1989) Chlamydial disease pathogenesis: the 57-kD chlamydial hypersensitivity antigen is a stress response protein *J. Exp. Med.* 170:1271-1283. Similarly: Morrison et al. (1989) Chlamydial disease pathogenesis: ocular hypersensitivity elicited by a genus-specific 57-kD protein. *J. Exp. Med.* 169:663-675
30 Marques et al. (1998) Mapping and Identification of the Major Cell Wall-Associated Components of *Mycobacterium leprae*. *Infect. Immun.* 66: 2625-2631.
31 Caldas et al. (1998) Chaperone properties of bacterial elongation factor EF-Tu. *J. Biol. Chem.* 273:11478-82
32 Oliveira & Splitter (1996) Immunization of mice with recombinant L7/L12 ribosomal protein confers protection against *Brucella abortus* infection. *Vaccine* 14:959-62

What is claimed is:

1. A method of eliciting a *Chlamydia trachomatis*-specific immune response in a patient, the method comprising the step of administering to the patient an effective amount of an immunogenic composition consisting of an immunogenic protein comprising a *Chlamydia trachomatis* htrA protein having the N-terminal sequence as shown in SEQ ID NO: 3.

* * * * *